(12) United States Patent
Giorno

(10) Patent No.: US 9,707,059 B2
(45) Date of Patent: Jul. 18, 2017

(54) SELF-CLEARING SELF-CUTTING IMPLANT

(75) Inventor: Thierry Giorno, Boca Raton, FL (US)

(73) Assignee: Intra-Lock International, Inc., Boca Raton, FL (US)

(*) Notice: Subject to any disclaimer, the term of this patent is extended or adjusted under 35 U.S.C. 154(b) by 0 days.

(21) Appl. No.: 12/694,055

(22) Filed: Jan. 26, 2010

(65) Prior Publication Data

US 2010/0190138 A1 Jul. 29, 2010

Related U.S. Application Data

(60) Provisional application No. 61/147,630, filed on Jan. 27, 2009.

(51) Int. Cl.
*A61C 8/00* (2006.01)
*A61B 17/86* (2006.01)

(52) U.S. Cl.
CPC .......... *A61C 8/0022* (2013.01); *A61B 17/863* (2013.01); *A61B 17/8605* (2013.01)

(58) Field of Classification Search
CPC ..... A61C 8/0022; A61C 8/005; A61C 8/0089; A61C 8/006; A61C 8/0069; A61C 8/0025
USPC .................. 433/174, 172; 411/421, 309–311
See application file for complete search history.

(56) References Cited

U.S. PATENT DOCUMENTS

| | | | | |
|---|---|---|---|---|
| 1,465,148 A * | 8/1923 | Rosenberg | ..................... | 411/418 |
| 2,232,336 A * | 2/1941 | Meersteiner | ................. | 411/421 |
| 3,672,058 A * | 6/1972 | Nikoghossian | ............... | 433/174 |
| 3,850,074 A * | 11/1974 | Simons | ................... | B21H 3/027 |
| | | | | 411/416 |
| 3,868,871 A * | 3/1975 | Yankee | ..................... | B21K 5/20 |
| | | | | 72/469 |
| 3,911,781 A * | 10/1975 | Bappert | ......................... | 411/418 |
| 4,259,889 A * | 4/1981 | Capuano | ....................... | 411/417 |
| 4,406,623 A * | 9/1983 | Grafelmann et al. | ........ | 433/174 |
| 4,468,200 A * | 8/1984 | Munch | ................. | A61C 8/0022 |
| | | | | 433/174 |
| 4,842,467 A * | 6/1989 | Armstrong | .................... | 411/399 |
| 4,863,383 A * | 9/1989 | Grafelmann | .................. | 433/174 |
| 4,871,313 A * | 10/1989 | Maillefer | ...................... | 433/225 |
| 5,088,926 A * | 2/1992 | Lang | ............................. | 433/173 |
| 5,110,245 A * | 5/1992 | Hiroyuki | ....................... | 411/421 |
| 5,676,545 A * | 10/1997 | Jones | ........................... | 433/165 |
| 5,702,445 A * | 12/1997 | Br.ang.nemark | .............. | 606/60 |
| 5,759,003 A * | 6/1998 | Greenway et al. | ........... | 411/421 |
| 5,984,681 A * | 11/1999 | Huang | ................... | A61C 8/001 |
| | | | | 433/173 |
| 6,102,703 A * | 8/2000 | Day | ............................. | 433/174 |
| 6,158,939 A * | 12/2000 | Grossberndt et al. | ........ | 411/411 |
| 6,273,722 B1 * | 8/2001 | Phillips | ......................... | 433/174 |
| 6,604,945 B1 * | 8/2003 | Jones | ........................... | 433/173 |
| 6,899,500 B2 * | 5/2005 | LeVey et al. | ................ | 411/411 |
| 7,070,376 B1 * | 7/2006 | Toback | ........................ | 411/82.2 |

(Continued)

OTHER PUBLICATIONS

Freitas et al., "The effect of implant design on insertion torque and immediate micromotion", Clinical Oral Implants Research, 2011, pp. 1-6.

*Primary Examiner* — Cris L Rodriguez
*Assistant Examiner* — Matthew Saunders
(74) *Attorney, Agent, or Firm* — Reising Ethington P.C.

(57) ABSTRACT

The invention relates to bone implants, namely screw-type implants and, more particularly, to a self tapping dental implant having at least two helical grooves running in opposite directions around the implant.

10 Claims, 7 Drawing Sheets

(56) References Cited

U.S. PATENT DOCUMENTS

| | | | |
|---|---|---|---|
| 7,156,600 B2* | 1/2007 | Panasik et al. | 411/411 |
| 7,214,020 B2* | 5/2007 | Suzuki | 411/417 |
| 7,806,693 B2* | 10/2010 | Hurson | A61C 8/0025 433/174 |
| 2004/0121289 A1* | 6/2004 | Miller | 433/174 |
| 2006/0127193 A1* | 6/2006 | Akaki et al. | 408/224 |
| 2008/0118893 A1* | 5/2008 | Armellini | A61K 9/0063 433/174 |
| 2008/0260493 A1* | 10/2008 | Kato | 411/378 |
| 2009/0220914 A1* | 9/2009 | Gershenzon | 433/174 |
| 2010/0240010 A1* | 9/2010 | Holmstrom | A61C 8/0022 433/174 |

* cited by examiner

US 9,707,059 B2

SELF-CLEARING SELF-CUTTING IMPLANT

This application claims priority to provisional application Ser. No. 61/147,630 filed on Jan. 27, 2009, the contents of which are expressly incorporated herein by reference.

FIELD OF INVENTION

The invention relates to bone implants, namely screw-type implants and, more particularly, to a self tapping dental implant having at least two helical grooves running in opposite directions around the implant.

BACKGROUND OF THE INVENTION

Implants for insertion into living bone, including screw type implants are widely used and are well known in the art. Such implants may be used in dentistry or orthopedics. The screw tapping implants generally fall into the category of self-tapping implants and non-self tapping implants. Non-self tapping implants are merely threaded and are screwed into the bone after it is separately drilled and tapped. Self tapping implants contain cutting threads analogous to those in a metal tap which cut threads into the bone when inserted in a drilled hole that is smaller than the self tapping implant diameter. The basic structure of both types of implants comprise a generally cylindrical main body that has a set of external screw threads on the outer surface which engage with threads cut into the bone. The engagement of the threads provides for initial stabilization for the implant. With both types of implants, long term stability is provided by growth of new bone around the implant. A non self-tapping implant is usually tapered at the end which is inserted into the bone. The other end of both implants contains a means for attaching a dental prosthesis such as a tooth and is often threaded to facilitate attachment of the prosthesis.

Self-tapping implants usually contain a more pronounced taper at the end of the implant on which the cutting threads of the tap portion of the implant are disposed.

Self tapping devices of the prior art suffer from a number of drawbacks. The thread cutting abilities of present devices are limited due to the thickness of the threads which creates large amounts of bone chips as part of the cutting process. Current designs are unable to effectively clear these bone chips from the hole. This results in an increase in the torque required to seat a self tapping implant. The increase in torque adds to patient discomfort and may also lead to breakage of the threads cut in the bone. The inability of the implant to clear debris can also prevent a surgeon from properly seating an implant. The seating and insertion torque problems increase as the length of the implant increases.

The art contains examples of implant designs having grooves within the cutting surfaces for removing debris.

Published United States patent application US20080187886A1 discloses a self tapping dental implant having a vertical groove for collecting debris.

Published United States patent application US20080160483A1 discloses a self tapping implant having a vertical groove for collecting debris.

Published United States patent application US20080131840A1 discloses a self tapping implant having a groove for holding debris.

Published United States patent application US20080081316A1 discloses a self tapping implant having a vertical groove for containing debris.

Published United States patent application US20080038693A1 discloses a self tapping implant having a vertical groove for containing debris.

United States patent U.S. Pat. No. 7,281,925 and published United States patent application US20080032264A1 disclose a self tapping implant having a groove cut within and parallel to the self tapping threads for containing debris.

Published United States patent application US20080014556A1 discloses a self tapping implant having a groove running with the threads for containing debris.

United States patent U.S. Pat. No. 7,273,373 discloses a self tapping implant having a groove for containing debris and protrusions to aid in anchoring.

Published United States patent application US20070190491A1 discloses a self tapping implant which is out of round and has breaks in the self tapping threads for passage of debris.

Published United States patent application US20070099153A1 discloses a self tapping implant having a substantially vertical groove in the self tapping threads for passage of debris.

Published United States patent application US20040121289A1 discloses a self tapping implant having a substantially vertical groove running in an opposite direction to the cutting threads for passage of debris.

United States patent U.S. Pat. No. 6,604,945 discloses a self tapping implant having a substantially vertical groove running for passage of debris.

Published United States patent application US20020102518A1 discloses an implant having a vertical groove for passage of debris.

United States patent U.S. Pat. No. 6,273,722 discloses an implant with helices running in opposite directions. However, this is not a self tapping implant.

United States patent U.S. Pat. No. 5,984,681 discloses a self tapping implant having open threads and a separate anchor.

United States patent U.S. Pat. No. 5,871,356 discloses an implant having vertical grooves for the passage of debris.

United States patent U.S. Pat. No. 5,601,429 discloses an implant having grooves for clearing debris running in the same direction as the cutting grooves Despite the above examples, there is still a need in the art for a self threading implant which is easy to install yet offers acceptable holding power.

OBJECTIVE OF THE INVENTION

It is an object of this invention to provide an improved self tapping implant having reduced torque for insertion and an increased load bearing surface at the time of insertion.

SUMMARY OF THE INVENTION

The present invention comprises a self tapping implant which requires substantially less torque to install than a traditional self tapping implant having full screw threads. The reduction in effort is achieved by the inclusion of at least one cutting surface on each rotation of the thread and by including a spiral groove which runs in an opposite direction to the threads. This enables the implant of the present invention to corkscrew into an opening instead of cutting course threads.

Implant designs of the present invention generate significantly less bone debris that the "classic tap cutting grooves". In the present invention, debris, are evenly distributed across the implant body length, rather than "collected" and compressed into either the grooves of the tap or the bottom of the hole in which the implant is being inserted.

According to one embodiment the implant comprises a substantially cylindrical body 1 having a proximal end 2 and a distal end 3. The body contains at least one external helical thread 9 which runs from the distal end 3 to the proximal end 2. The helical thread 9 maybe right or left handed and contains at least one cutting edge 6 for each turn of the cutting head. The implant further comprises a second helix 10 running in the opposite direction of the helical thread.

DETAILED DESCRIPTION OF THE INVENTION

The present invention comprises a self tapping implant which requires substantially less torque to install than devices currently in use. The reduction in effort is achieved by the inclusion of at least one cutting surface on each rotation of the thread and by including a spiral groove which runs in an opposite direction to the threads. This enables the implant of the present invention to corkscrew into an opening instead of cutting course threads.

Figure 1:
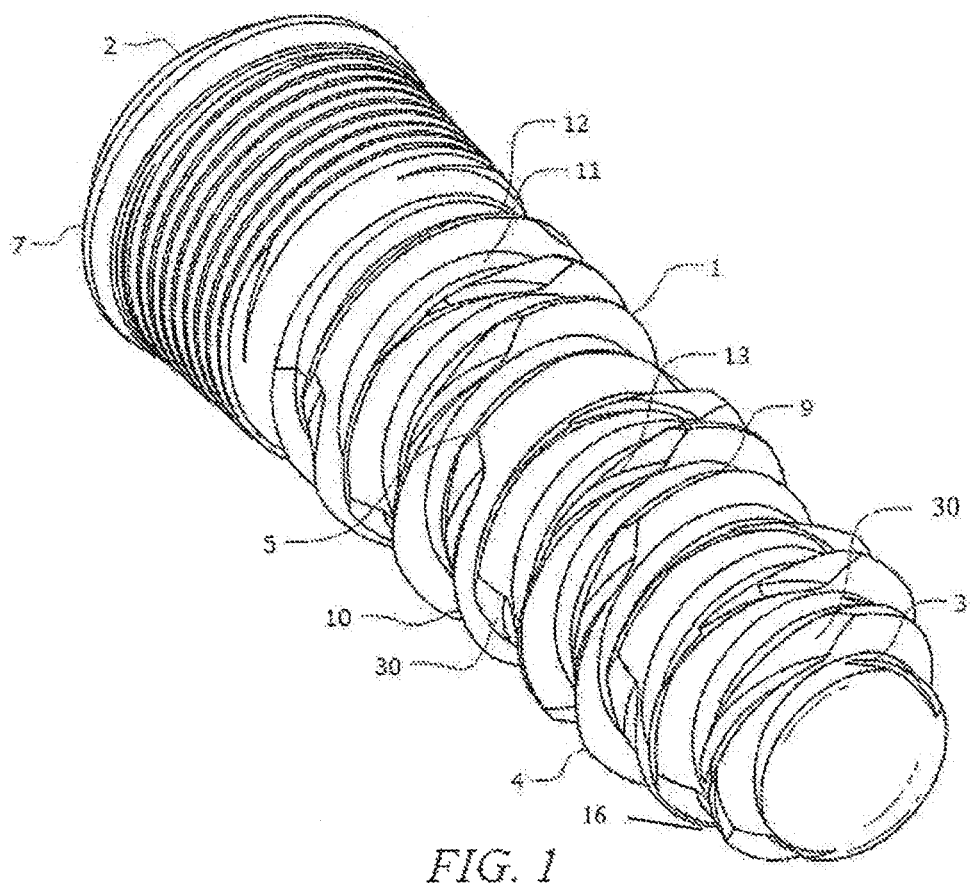
FIG. 1 is a perspective view of a dental implant according to one embodiment.
Figure 2:
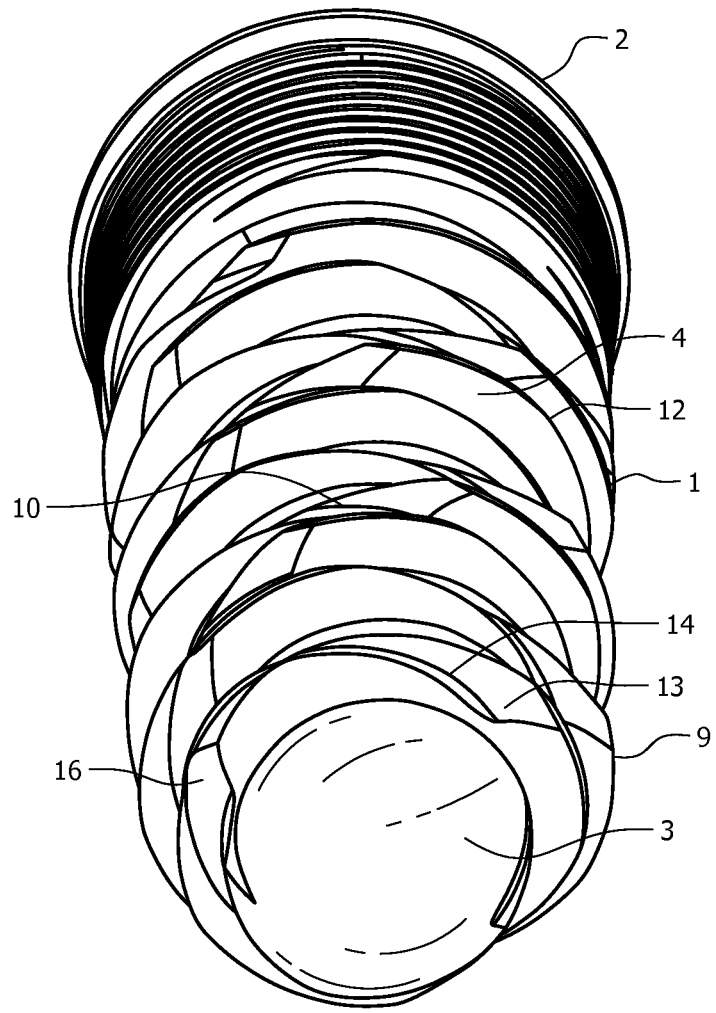
FIG. 2 is a distal end view of a dental implant according to one embodiment.
Figure 3:
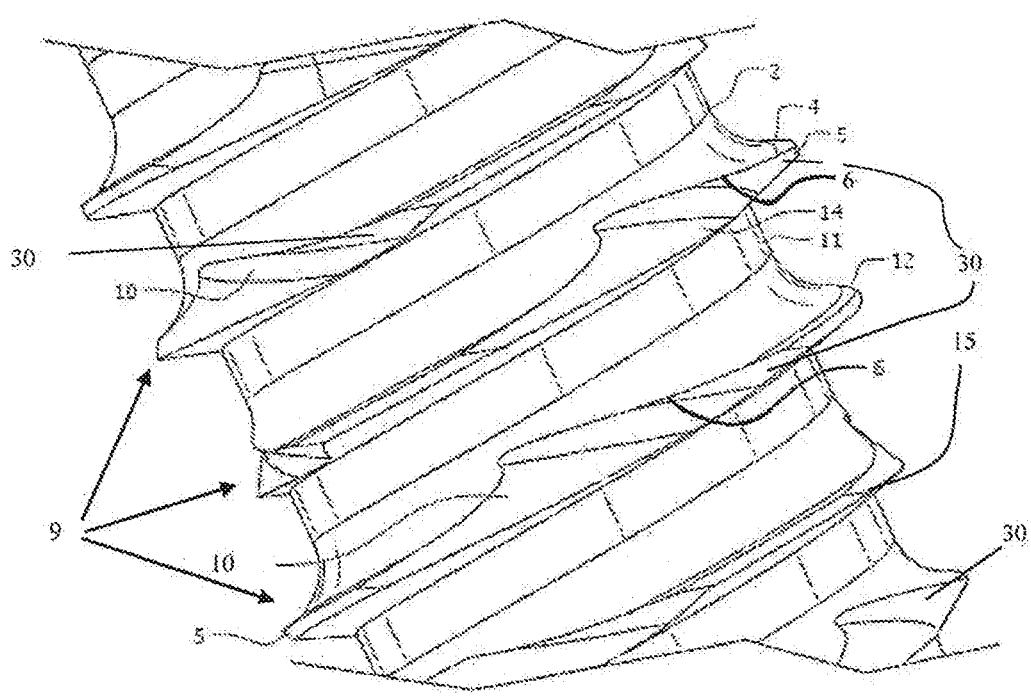
FIG. 3 is an expanded side view of the implant in FIGS. 1 and 2.
Figure 4:
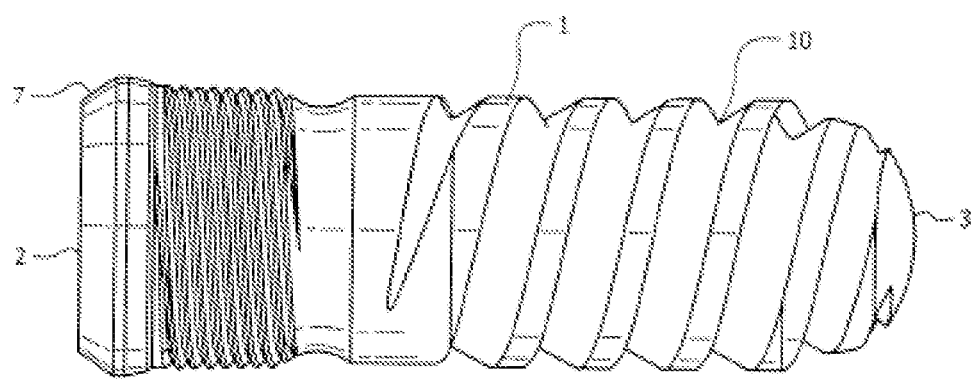
FIG. 4 is a side view showing a secondary helix.

Referring to FIGS. 1-3, according to one dental implant embodiment, the implant comprises a substantially cylindrical body 1 having a proximal end 2 and a distal end 3. The proximal end contains a prosthetic platform 7 onto which a prosthesis will be fitted. The body contains at least one external helical thread 9 which runs from the distal end 3 to the proximal end 2. The helical thread 9 maybe right or left handed and contains at least one cutting edge 6 for each turn of the cutting head. The implant further comprises a second helix 10 running in the opposite direction of the helical thread. The second helix 10 is cut at approximately the same depth as the external helical thread 9. The second helix can be seen more clearly in FIG. 4 in which the helical thread 9 has been omitted for clarity.

The helical thread 9 is further comprised of an inner, or minor, diameter 11 and an outer, or major, diameter 12. The outer diameter 12 forms a ridge 4 having a plateau 5 on the outermost thread surfaces, which engages with the bone during insertion. It is preferred that the plateau 5 be as narrow as possible subject to the structural limitations of the material comprising the implant. Thinner diameters allow for smaller pilot holes, easier drilling and reduce the torque required for insertion. Larger plateaus may be required for softer bone.

The thread pitch 15 is not critical to the invention and may be increased or decreased depending on the mechanical needs for the application. Thread pitch can be constant or variable.

The helical thread 9 comprises a recess 13 and a beveled surface 14. The angle of the bevel is not critical but should be as narrow as possible to facilitate cutting into the bone, but not so narrow that the structural integrity of the cutting surface and thread is compromised.

The cutting edge 6 is formed by cutting the second helix 10 into the body of the implant and is contiguous with the helical thread 9. In a preferred embodiment the thread 9 has a chamfer 30 adjacent the cutting edge. The chamfer 30 makes contact with the bone following the cutting edge 6. The second helix 10, in addition to creating the cutting edge 6, also serves to assist in clearing bone debris created by the cutting edge.

The main body 1 may be straight or tapered, with a straight body being most preferred. When the main body 1 is straight it is preferred that the initial turn of the helix 16 be of a smaller diameter than the rest of the main body 1 to facilitate easy insertion into the pilot hole.

In yet another embodiment a secondary thread (not shown) may be included inside the helical thread 9.

Figure 5:
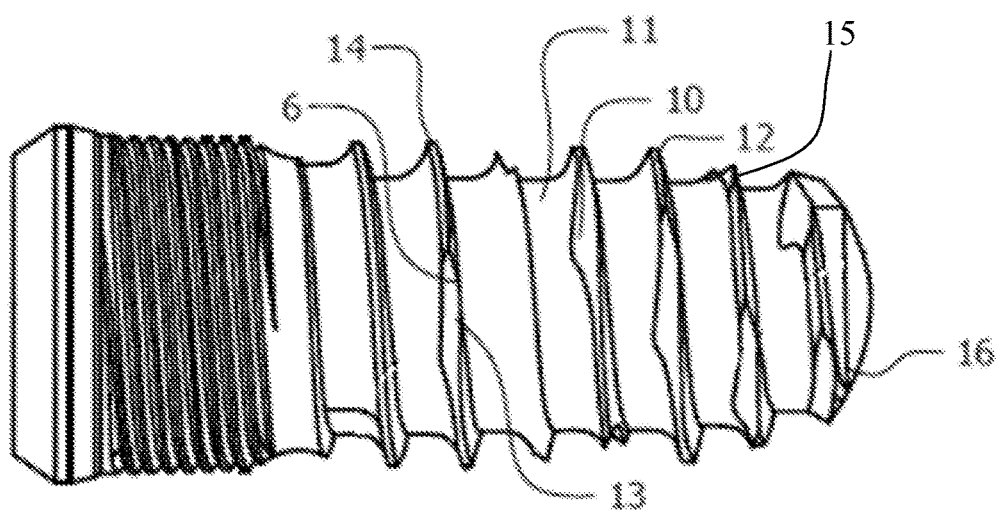
FIG. 5 is a side view showing the details for a particular embodiment of a dental implant.

FIG. 5 is an engineering drawing of one embodiment in which the implant is 4 mm in length and has an outer diameter 12 of 0.1540 cm and an inner diameter 11 of 0.12 cm. The distance between the leading edges of the thread 9 is 0.0354 and each thread has a 15 degree undercut on the bottom side and a cut having a radius of 0.015 cm on the top side. The secondary helix 10 is cut at a depth of 0.130 cm. The top of the secondary helix is cut at a 60 degree angle and the bottom of the helix is cut at a 15 degree angle with a radius of 0.005 cm in the valley.

One of skill in the art will appreciate that the surface of the implant can be further processed to aid in growth of new bone around it. Such processing can include the use of coatings or modifying the surface textures of the implant as is known in the art.

The prosthetic platform may be structured to accommodate any form of implant. It can comprise internal threads (not shown) which are inside the body of the implant or external threads (not shown) or comprise any type of stud or ball upon which a prosthesis can be mounted. The thread pitch is not critical and may be selected for the application. In yet other embodiments, the implant may contain surfaces suitable for bonding the prosthesis to the implant.

The implant of the present invention is used in a conventional manner. The dentist or surgeon will drill a pilot hole for the implant. The implant is attached to an insertion tool and turned into the pilot hole. Upon turning, the cutting edge 6 will cut a groove into the bone into which the helical thread 9 will follow. Because cutting edge 6 has a sharp edge leading into a narrow plateau on the helical thread 9, less bone debris is generated. This debris is pushed towards the proximal end of the body through the second helical groove 10. This movement of debris keeps the pilot hole relatively free from debris thereby preventing debris from filling the pilot hole and jamming the implant. This reduces incidences of the implant prematurely bottoming out in the pilot hole because of debris filling the hole and reduces the debris caught in the helical groove thereby reducing friction on the cutting surfaces which reduces the torque required for insertion.

Manufacturing

Implants of the present invention can be manufactured from any structural material suitable for dental implants, including but not limited to stainless steels, titanium, ceramics, polymers and any other material with appropriate mechanical characteristics which is biocompatible. Titanium is most preferred. Implants of the present invention can be readily manufactured using a modern lathe capable of cutting screw threads. The unfinished stock is mounted in the lathe at the proximal end. The cutting blade of the lathe cuts a helical groove in the stock leaving the desired primary thread. The direction of rotation is then changed and the desired secondary helical groove is cut across the primary thread thereby creating the cutting surfaces. The shape of the helices are determined by the cutting head on the lathe and different cutting heads can be used to create different helices. It will be appreciated that both straight and tapered implants can be created in this manner.

Alternatively, depending on the manufacturing materials, the implant can be formed by passing the stock comprising the body through one or more cutting dies as is known in the art or by the use of molds or forging. For implants made of plastics, ceramics or polymers, molding is the preferred method of manufacture.

As long as the properties of the implant materials are taken into account any thread pitch, thread thickness and cutting edge are possible up the point where the material is too thin to support the load placed on it. Threads and cutting edges that are too thin may break under higher torques or distort during insertion.

Reduction of Insertion Torque

Experiments were performed comparing the insertion of the implant of the present invention with an equal diameter implant using classic cutting flukes. In the test protocol, high density polyurethane was used to simulate bone. A block of polyurethane was secured to a work station and 3.2 mm holes drilled in the block. The implants were then inserted using a digital torque wrench (Tohnichi, Japan). The insertion torque was recorded in Newton centimeters after each complete turn and the data recorded. These data are shown in Tables 1 and 2 below.

TABLE 1

Insertion Torque for Improved Cutting Flukes
Insertion torque for implant having improved
cutting flutes), Ø.125 (3.2 mm) hole

| # of turns | Sample 1 | Sample 2 | Sample 3 | Sample 4 | Sample 5 | Average |
|---|---|---|---|---|---|---|
| 1 |  | 6 | 6 | 6 | 6 | 6 |
| 2 |  | 10 | 10 | 9 | 6 | 8.75 |
| 3 |  | 12 | 12 | 12 | 9 | 11.25 |
| 4 |  | 13 | 14 | 15 | 10 | 13 |
| 5 |  | 15 | 16 | 17 | 12 | 15 |
| 6 |  | 16 | 18 | 19 | 14 | 16.75 |
| 7 |  | 17 | 19 | 22 | 16 | 18.5 |
| 8 |  | 20 | 21 | 23 | 19 | 20.75 |
| 9 |  | 22 | 23 | 23 | 20 | 22 |
| 10 |  | 26 | 26 | 26 | 22 | 25 |
| 11 |  | 27 | 28 | 29 | 23 | 26.75 |
| 12 |  | 31 | 28 | 31 | 29 | 29.75 |
| 13 |  | 42 | 45 | 47 | 45 | 44.75 |

TABLE 2

Insertion Torque for Classic Cutting Flutes
Insertion torque for implant w/classic cutting flutes Ø.125 (3.2 mm) hole

| # of turns | Test 1 | Test 2 | Test 3 | Test 4 | Average |
|---|---|---|---|---|---|
| 1 | 4 | 6 | 5 | 7 | 5.5 |
| 2 | 8 | 10 | 9 | 9 | 9 |
| 3 | 10 | 11 | 11 | 10 | 10.5 |
| 4 | 12 | 13 | 14 | 13 | 13 |
| 5 | 16 | 18 | 15 | 16 | 16.25 |
| 6 | 18 | 19 | 19 | 19 | 18.75 |

TABLE 2-continued

Insertion Torque for Classic Cutting Flutes
Insertion torque for implant w/classic cutting flutes Ø.125 (3.2 mm) hole

| # of turns | Test 1 | Test 2 | Test 3 | Test 4 | Average |
|---|---|---|---|---|---|
| 7 | 22 | 22 | 24 | 23 | 22.75 |
| 8 | 25 | 27 | 29 | 27 | 27 |
| 9 | 32 | 33 | 35 | 32 | 33 |
| 10 | 37 | 41 | 42 | 38 | 39.5 |
| 11 | 44 | 49 | 51 | 47 | 47.75 |
| 12 | 54 | 62 | 65 | 59 | 60 |
| 13 | 67 | 78 | 80 | 77 | 75.5 |

Figure 6:
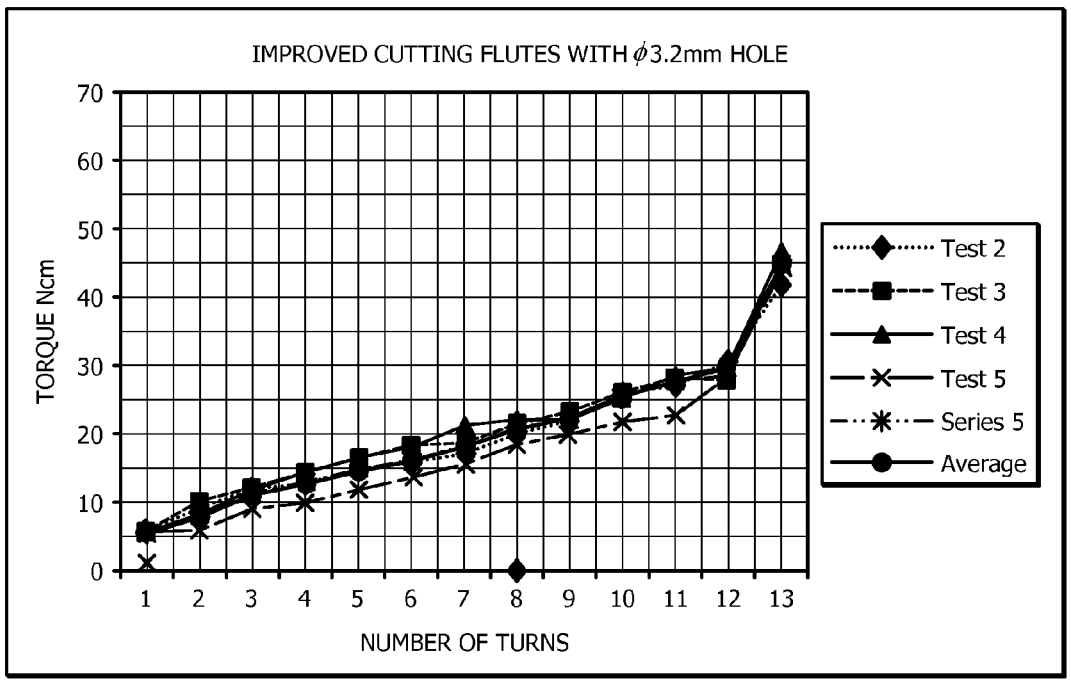
FIG. 6 is a graph of insertion torque for a dental implant according to one embodiment.
Figure 7:
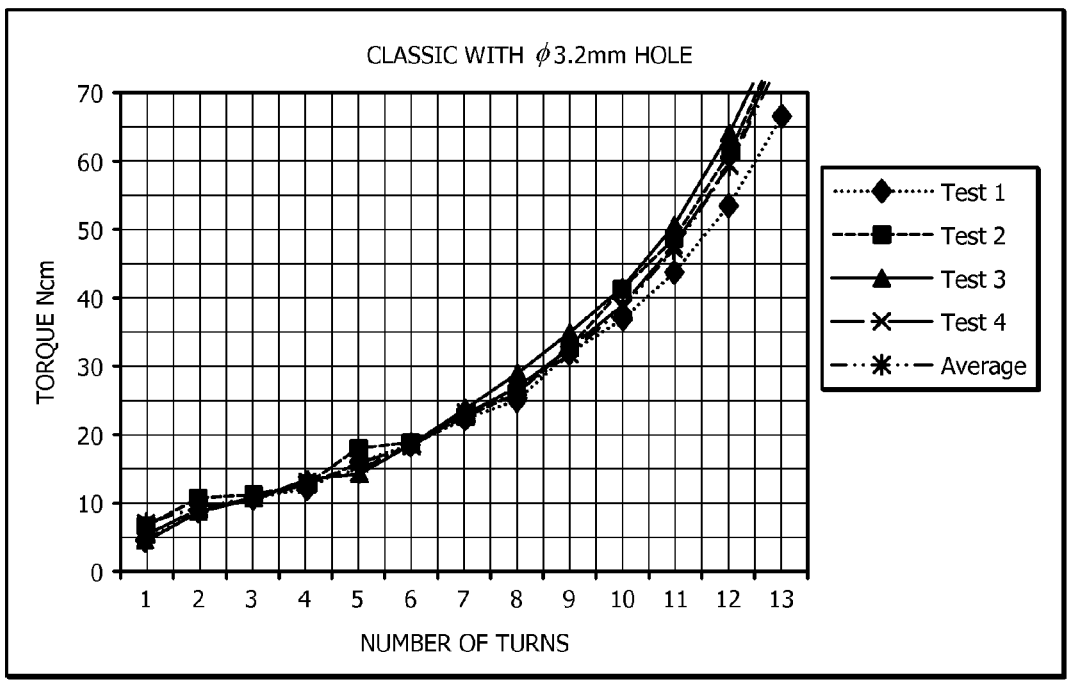
FIG. 7 is a graph of insertion torque for a dental implant using prior art designs.

The data in Tables 1 and 2 show that the insertion torque of the implant of the present invention is comparable to the insertion torque of the classic design for shallower insertion depths. However, as depth of insertion increases, the classic implant design requires significantly more torque to insert in contrast to the implant of the present invention. These same data are graphed in FIGS. 6 and 7.

Figure 8:
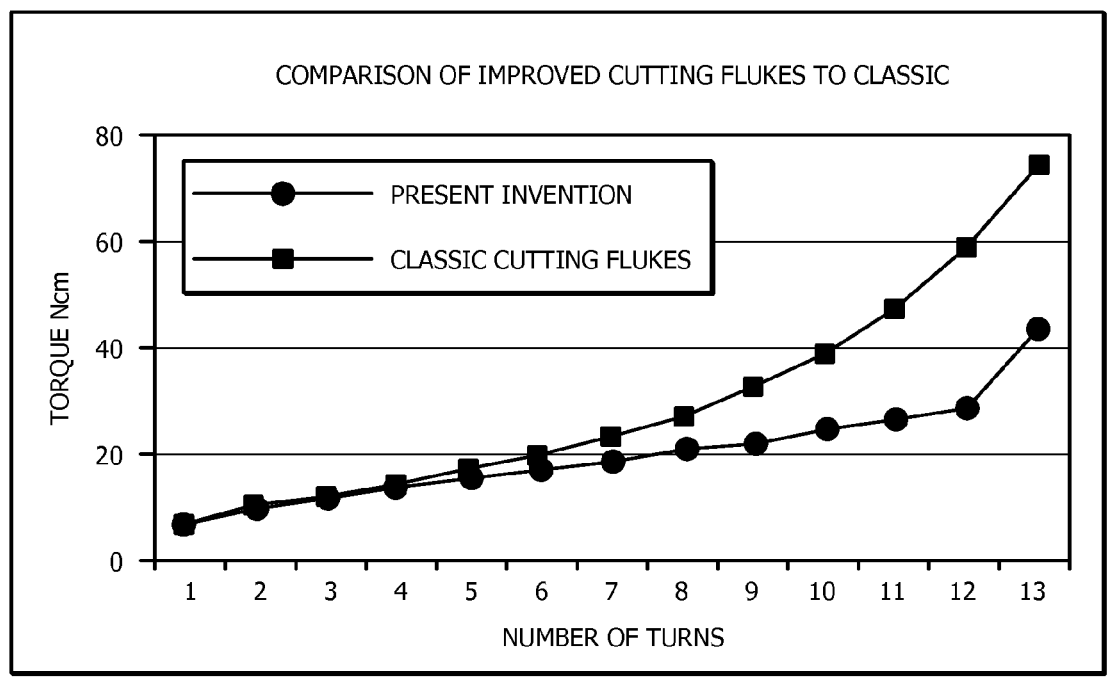
FIG. 8 is a graph comparing the average insertion torque of the present invention to a prior art design.

Referring to FIG. 8 which is a line graph comparing the average torques recorded for each turn in Tables 1 and 2 above. FIG. 8 shows that the cutting flukes of the present invention require substantially less torque as the implant is turned deeper into the socket. The present invention only required an average of 16.75 Ncm of torque during insertion of turn 8 compared with 27 Ncm of torque for the version of the implant having classic cutting flukes. The results are even more dramatic at 13 turns in which the present invention only required 44.75 Ncm of torque compared to 75.5 Ncm of torque for the version of the implant having classic cutting flukes. The present invention will allow easier insertion by a surgeon and reduce the discomfort felt by the patient.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

I claim:

1. A self-tapping implant comprising:
    a body comprising a generally cylindrical portion having an outer circumference;
    a helical thread wound around at least a portion of the outer circumference;
    first and second blades formed at spaced locations in the thread and each having an arcuate cutting edge that curves helically aft and radially outward from adjacent a minor thread diameter to merge with a thread ridge at a major thread diameter, thereby providing a gradual arcuate slashing-type cutting action as the thread travels helically forward along a helical insertion path when the implant is being driven into bone tissue, a forward surface of the first blade being in helical alignment with a forward surface of the second blade, the helical alignment of the forward blade surfaces being in opposite handedness to the helical thread.

2. The implant of claim 1 including a plurality of blades formed in the thread at spaced locations along the thread and having respective arcuate cutting edges that curve helically aft and radially outward from adjacent respective minor thread diameters and merge at respective major thread diameters with the thread ridge at respective spaced locations along the thread ridge.

3. The implant of claim 2 in which the plurality of blades are formed at locations spaced along the thread at one thread-turn intervals.

4. The implant of claim 2 in which the plurality of blades are arrayed in a helical pattern of opposite handedness to that of the helical thread.

5. The implant of claim 4 in which the plurality of blades are formed at respective intersections where the helical thread is crossed by a helical groove that is formed into the thread and that has a handedness opposite that of the helical thread.

6. The implant of claim 1 in which the generally cylindrical portion of the body includes a tapered section.

7. The implant of claim 1 in which the generally cylindrical portion of the body includes a straight section.

8. The implant of claim 1 in which the implant is a dental implant.

9. The implant of claim 1 in which the implant is a bone screw.

10. The implant of claim 5 in which the body, the thread, and the blades of the plurality of blades are shaped and positioned such that an amount of torque required to insert the implant in a polyethylene block is less than 17 NCm after 6 turns and less than 20 NCm after 7 turns.

* * * * *

UNITED STATES PATENT AND TRADEMARK OFFICE
CERTIFICATE OF CORRECTION

PATENT NO. : 9,707,059 B2
APPLICATION NO. : 12/694055
DATED : July 18, 2017
INVENTOR(S) : Thierry Giorno It is certified that error appears in the above-identified patent and that said Letters Patent is hereby corrected as shown below:

In the Specification

In Column 4, Line 27, please delete -- "cut at a depth of 0.130 cm." -- and add "cut at a depth of 0.0130 cm."

Signed and Sealed this
Twentieth Day of March, 2018

Andrei Iancu
*Director of the United States Patent and Trademark Office*